US010881278B2

(12) United States Patent
Wake et al.

(10) Patent No.: US 10,881,278 B2
(45) Date of Patent: Jan. 5, 2021

(54) ENDOSCOPE APPARATUS AND ENDOSCOPE SYSTEM PROVIDING ANGULAR ORIENTATION BETWEEN OVERTUBE AND ENDOSCOPE INSERTION SECTION INSERTED IN OVERTUBE

(71) Applicant: OLYMPUS CORPORATION, Tokyo (JP)

(72) Inventors: Fuminori Wake, Hachioji (JP); Kazuhiko Hino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 489 days.

(21) Appl. No.: 15/826,827

(22) Filed: Nov. 30, 2017

(65) Prior Publication Data

US 2018/0084974 A1    Mar. 29, 2018

Related U.S. Application Data

(63) Continuation of application No. PCT/JP2016/064984, filed on May 20, 2016.

(30) Foreign Application Priority Data

Jun. 3, 2015   (JP) .................................. 2015-113341

(51) Int. Cl.
*A61B 1/00*         (2006.01)
*A61B 1/015*        (2006.01)
(Continued)

(52) U.S. Cl.
CPC ...... *A61B 1/00154* (2013.01); *A61B 1/00089* (2013.01); *A61B 1/00091* (2013.01); (Continued)

(58) Field of Classification Search
None
See application file for complete search history.

(56) References Cited

U.S. PATENT DOCUMENTS 4,971,034 A * 11/1990 Doi .................... A61B 1/00068
                                                    600/104
5,725,474 A *  3/1998 Yasui ................. A61B 1/00091
                                                    600/121
(Continued)

FOREIGN PATENT DOCUMENTS

CN      102578999 A    7/2012
JP    2004-267583 A    9/2004
(Continued)

OTHER PUBLICATIONS

Machine English Translation of JP2014-018563a Hirata Yasuo, 2014 (Year: 2014).*

(Continued)

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

The endoscope apparatus includes an endoscope insertion portion configured to be inserted into a subject and including a distal end portion, a distal end covering portion configured to cover at least an outer periphery of the distal end portion of the endoscope insertion portion and held by the distal end portion, a suction conduit provided with an opening in the distal end covering portion and configured to discharge a fluid including gas generated from an inside of the subject to outside of the subject via the opening, and a positioning portion configured to define a position of the opening of the suction conduit in a rotation direction with a long axis of the endoscope insertion portion as a center when the distal end (Continued)

covering portion is held by the distal end portion of the endoscope insertion portion.

15 Claims, 7 Drawing Sheets

(51) Int. Cl.
| | |
|---|---|
| *A61B 1/018* | (2006.01) |
| *A61B 1/05* | (2006.01) |
| *A61B 1/12* | (2006.01) |
| *A61B 1/005* | (2006.01) |
| *A61B 18/14* | (2006.01) |
| *A61B 18/08* | (2006.01) |
| *A61B 18/00* | (2006.01) |

(52) U.S. Cl.
CPC ...... *A61B 1/00094* (2013.01); *A61B 1/00101* (2013.01); *A61B 1/00117* (2013.01); *A61B 1/00119* (2013.01); *A61B 1/00135* (2013.01); *A61B 1/015* (2013.01); *A61B 1/018* (2013.01); *A61B 1/05* (2013.01); *A61B 1/126* (2013.01); *A61B 18/08* (2013.01); *A61B 18/1482* (2013.01); *A61B 18/1492* (2013.01); *A61B 1/0051* (2013.01); *A61B 2018/00172* (2013.01); *A61B 2018/00595* (2013.01); *A61B 2018/00982* (2013.01); *A61B 2218/007* (2013.01)

(56) References Cited

U.S. PATENT DOCUMENTS

| | | | | |
|---|---|---|---|---|
| 5,725,477 | A * | 3/1998 | Yasui | A61B 1/00091 600/121 |
| 2007/0249907 | A1* | 10/2007 | Boulais | A61B 1/05 600/179 |
| 2008/0021274 | A1* | 1/2008 | Bayer | A61B 1/0676 600/112 |
| 2008/0130108 | A1* | 6/2008 | Bayer | A61B 1/00096 359/489.07 |
| 2009/0156898 | A1* | 6/2009 | Ichimura | A61B 1/04 600/127 |
| 2015/0011831 | A1* | 1/2015 | Ouchi | A61B 1/015 600/159 |

FOREIGN PATENT DOCUMENTS

| | | |
|---|---|---|
| JP | 2011-067597 A | 4/2011 |
| JP | 2014-018563 A | 2/2014 |
| WO | WO 2011/024900 A1 | 3/2011 |

OTHER PUBLICATIONS

International Search Report dated Aug. 16, 2016 issued in PCT/JP2016/064984.

* cited by examiner

ENDOSCOPE APPARATUS AND ENDOSCOPE SYSTEM PROVIDING ANGULAR ORIENTATION BETWEEN OVERTUBE AND ENDOSCOPE INSERTION SECTION INSERTED IN OVERTUBE

CROSS REFERENCE TO RELATED APPLICATION

This application is a continuation application of PCT/JP2016/064984 filed on May 20, 2016 and claims benefit of Japanese Application No. 2015-113341 filed in Japan on Jun. 3, 2015, the entire contents of which are incorporated herein by this reference.

BACKGROUND OF INVENTION

1. Field of the Invention

The invention relates to an endoscope apparatus and an endoscope system capable of endoscopic treatment.

2. Description of the Related Art

Conventionally, endoscopes configured by having insertion portions in elongated tube shapes have been widely used in the medical field, and the industrial field, for example. Among the endoscopes, a medical endoscope that is used in the medical field is configured to be able to observe an organ or the like by the insertion portion being inserted into a subject, for example, a body cavity of a living body, and apply various kinds of treatments to the organ or the like in accordance with necessity by using a treatment instrument (forceps) inserted in a treatment instrument insertion channel (forceps channel) included in the endoscope. Further, an industrial endoscope that is used in the industrial field is configured to be able to perform observation, inspection and the like of a state in an object, for example, flaws and corrosion by inserting an insertion portion into the object, for example, an apparatus or a facility of a jet engine or plant piping.

In recent years, as procedures that are performed for the purpose of early cancer treatment, for example, among procedures of treatment and the like that are performed by using endoscope apparatuses and endoscope systems including endoscopes of this kind, a procedure called endoscopic mucosal resection (EMR) that cuts off a lesion portion by inserting a treatment instrument that is called a snare and is formed of a metal annular member into a body cavity via a treatment instrument insertion channel, putting the snare or the like on the lesion portion, and passing a high-frequency current to the snare or the like, and various procedures called endoscopic submucosal dissection (ESD) that similarly cuts off a lesion portion in a body cavity by using an exclusive treatment instrument such as a high-frequency electric knife, and the like have been carried out.

Here, when the procedure by the above described ESD is carried out, for example, in a process step of dissecting and coagulating a tissue in a body cavity by using a high-frequency electric knife, for example, mucus, fat, living tissue and the like in the body cavity vaporize by a high temperature of the high-frequency electric knife to be in a mist state, which is sometimes filled in the body cavity to hinder an observation field of view by the endoscope.

At the same time, liquid droplets and the like in a mist state including fat, living tissue and the like sometimes adhere to a surface of an observation window or the like that is provided on a distal end face of the endoscope. Then, an endoscopic image that is acquired and displayed sometimes becomes unclear.

In reality, the type of liquid droplets and the like in a mist state including fat, living tissue and the like cannot be cleaned easily even with an air feeding and liquid feeding function by gas, a liquid and the like for cleaning that are jetted from a nozzle and the like provided on the distal end face of the endoscope, for example. Accordingly, in the case like this, it has been necessary to remove the endoscope from the inside of the body cavity and clean the observation window and the like regularly, halfway through the procedure by ESD, for example.

Thus, in the conventional endoscope apparatus and endoscope system, a configuration is conceivable, in which when liquid droplets and the like in a mist state including fat and living tissue and the like are generated in a body cavity halfway through the procedure by the ESD, for example, the above described liquid droplets and the like in a mist state is sucked and discharged to outside via a treatment instrument insertion channel by operating a suction apparatus, for example.

The endoscope apparatus and the endoscope system with the configuration like this can suck the liquid droplets and the like in the mist state in the vicinity of the distal end opening of the treatment instrument insertion channel, out of the above described liquid droplets and the like in the mist state filled in the body cavity, but sometimes have difficulty in reliably sucking the liquid droplets and the like in the mist state in a position away from the treatment instrument inserting channel such as the vicinity of the observation window. Then, a possibility that the liquid droplets in the mist state adhere to the surface of the observation window and the like cannot be eliminated, and therefore, the endoscopic image cannot be prevented from becoming unclear.

Further, some of the conventional endoscope apparatuses and endoscope systems include an endoscope over tube (hereinafter, simply referred to as an over tube) through which a flexible endoscope is inserted, an attachment unit that is attached to a distal end of the endoscope or the like. In this case, Japanese Patent Application Laid-Open Publication No. 2011-67597 and the like have made various proposals of endoscope apparatuses each having a structure in which the above described over tube, the above described distal end attachment or the like is configured by being provided with a conduit, a distal end of the tube is connected to the conduit, a proximal end of the tube is configured by being connected to a suction apparatus, whereby when the above described suction apparatus is operated, the above described liquid droplets in the misty state and the like in the body cavity can be sucked via the above described tube from a vicinity of the distal end portion of the endoscope inserted into the body cavity.

SUMMARY OF THE INVENTION

An endoscope apparatus of one aspect of the present invention includes an endoscope insertion portion configured to be inserted into a subject and including a distal end portion, a distal end covering portion configured to cover at least an outer periphery of the distal end portion of the endoscope insertion portion and held by the distal end portion, a first conduit provided with an opening in the distal end covering portion, and configured to cause an inside of the subject and an outside of the subject to communicate with each other, and a positioning portion configured to define a position of the opening of the first conduit in a rotation direction with a long axis of the endoscope insertion portion as a center, when the distal end covering portion is held by the distal end portion of the endoscope insertion portion, wherein the endoscope insertion portion includes an observation optical system configured to acquire an optical image of the inside of the subject, and a second conduit configured to cause a proximal end side and a distal end side of the endoscope insertion portion to communicate with each other, and cause a treatment instrument to be inserted through the inside of the subject, and when a second straight line is defined, which passes through a median point between an optical axis of the observation optical system and a center axis of the second conduit and is orthogonal to a first straight line that connects the optical axis of the observation optical system and the center axis of the second conduit in the distal end portion of the endoscope insertion portion, the positioning portion positions a position of the opening of the first conduit with respect to the distal end portion of the endoscope insertion portion so that the opening of the first conduit is located at a side facing the second conduit, with the second straight line between the second conduit and the opening of the first conduit.

Further, an endoscope system of one aspect of the present invention includes an endoscope insertion portion configured to be inserted into a subject and including a distal end portion, a distal end covering portion configured to cover at least an outer periphery of the distal end portion of the endoscope insertion portion and held by the distal end portion, a first conduit provided with an opening in the distal end covering portion and configured to cause an inside of the subject and an outside of the subject to communicate with each other, a positioning portion configured to define a position of the opening of the first conduit in a rotation direction with a long axis of the endoscope insertion portion as a center, when the distal end covering portion is held by the distal end portion of the endoscope insertion portion, a second conduit configured to cause a proximal end side and a distal end side of the endoscope insertion portion to communicate with each other, a treatment instrument configured to be inserted into the subject from the outside of the subject via the second conduit, a cautery apparatus configured to cauterize a part of the subject by giving energy to the treatment instrument in the subject, and a suction apparatus to which the first conduit connects to discharge mist generated when the cautery apparatus cauterizes a part of the subject to the outside of the subject from the inside of the subject via the first conduit, wherein the endoscope insertion portion includes an observation optical system configured to acquire an optical image of the inside of the subject, and when a second straight line is defined, which passes through a median point between an optical axis of the observation optical system and a center axis of the second conduit and is orthogonal to a first straight line that connects the optical axis of the observation optical system and the center axis of the second conduit in the distal end portion of the endoscope insertion portion, the positioning portion positions a position of the opening of the first conduit with respect to the distal end portion of the endoscope insertion portion so that the opening of the first conduit is located at a side facing the second conduit, with the second straight line between the second conduit and the opening of the first conduit.

DETAILED DESCRIPTION OF THE PREFERRED EMBODIMENT(S)

Figure 1:
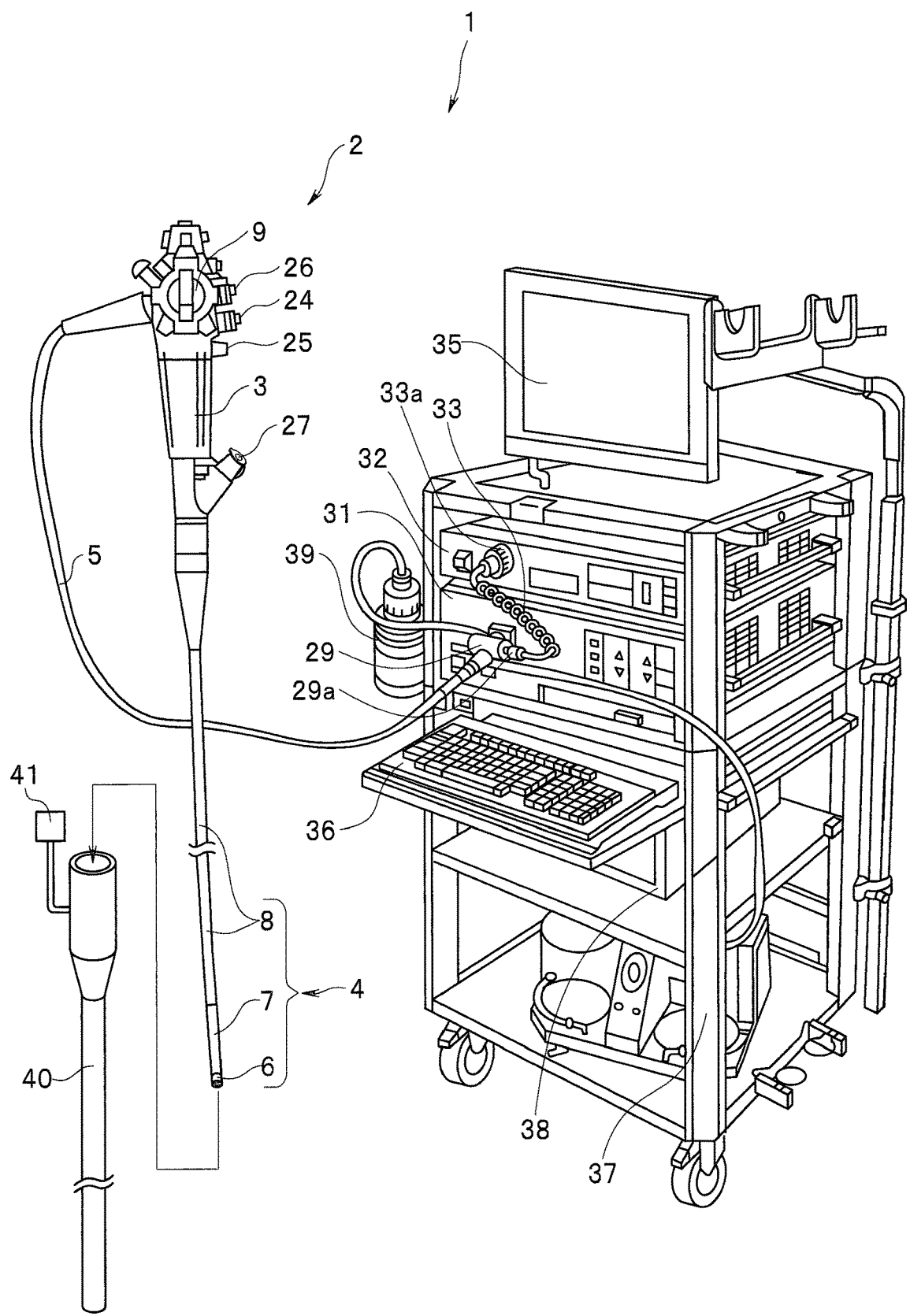
FIG. 1 is a schematic configuration view of an endoscope system including an endoscope of a first embodiment of the present invention.

Hereinafter, the present invention will be described based on illustrated embodiments. The respective drawings for use in the following explanation schematically illustrate, and illustrate by causing size relations, reduced scales and the like of the respective members at each of the respective components to be different in some cases in order to illustrate the respective components in such sizes that the respective components are recognizable in the drawings. Accordingly, the present invention is not limited only to the illustrated modes, in terms of the numbers and quantities of the components, shapes of the components, ratios of the sizes of the components, the relative positional relationship among the respective components and the like which are illustrated in the respective drawings.

First Embodiment

At first, a schematic configuration of an entire endoscope system including an endoscope apparatus of a first embodiment of the present invention will be described hereunder with use of FIG. 1. FIG. 1 is a schematic configuration view of an endoscope system including an endoscope of the first embodiment of the present invention.

An endoscope system 1 including the endoscope apparatus of the present embodiment is configured by an endoscope 2, a light source apparatus 31, a video processor 32, a display apparatus 35, a keyboard 36 that is external input equipment, a rack 37, the other medical external equipment 38 such as a recording apparatus and a cautery apparatus, an endoscope over tube 40 as a distal end covering portion, a suction apparatus 41 and the like.

The endoscope 2 is configured by an operation portion 3, an insertion portion (an endoscope insertion portion) 4, a universal cord 5 and the like. Among these portions, the insertion portion 4 is a component unit in an elongated tube shape formed by a distal end portion 6, a bending portion 7 and a flexible tube portion 8 being connectively provided in sequence from a distal end. A proximal end of the insertion portion 4 is connectively provided at a distal end of the operation portion 3. The insertion portion 4 is a component portion that is inserted into a lumen, that is, into a body cavity of a subject at a time of use of the endoscope 2. Note that in the present embodiment, the endoscope apparatus is configured by the above described endoscope 2, the endoscope over tube 40 that is the distal end covering portion and the suction apparatus 41. A detailed configuration of the endoscope apparatus will be described later.

Figure 2:
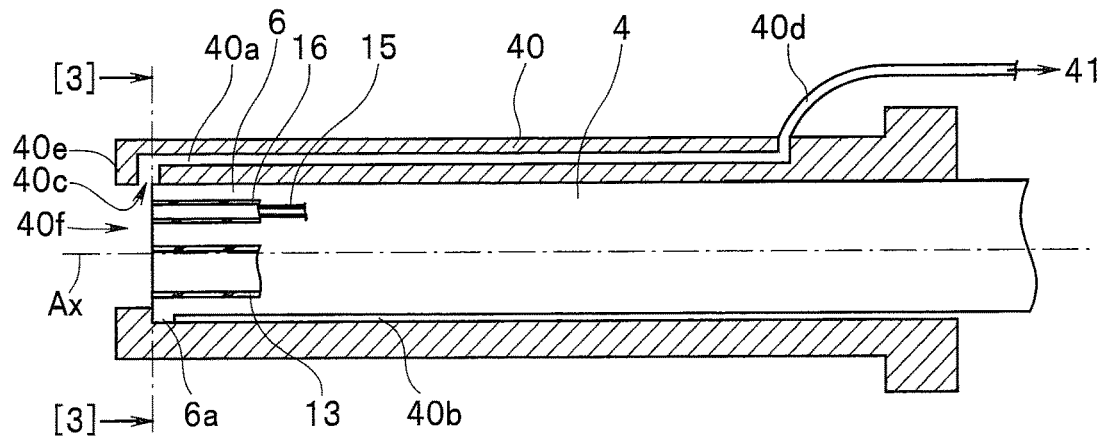
FIG. 2 is a schematic sectional view along a long axis Ax of an endoscope apparatus of the first embodiment of the present invention.

The flexible tube portion 8 of the insertion portion 4 is formed by a long tubular member that has flexibility and is hollow, has a proximal end side connectively provided at the distal end of the above described operation portion 3, and has a distal end side connectively provided at the proximal end of the bending portion 7. Inside the flexible tube portion 8, various signal lines and light guide cables (not illustrated) including an image pickup cable 16 (Not illustrated in FIG. 1. Refer to FIG. 2 described later) extended from the distal end portion 6 and the like, a treatment instrument channel 13 (Not illustrated in FIG. 1. Refer to FIG. 2 described later) and the like are inserted and disposed.

The bending portion 7 is a component portion that is formed to be bendable in a vertical direction and a lateral direction with respect to an insertion axis of the insertion portion 4. As for a configuration of the bending portion 7 itself, a configuration in a mode configured by connecting a plurality of bending pieces, for example, is applied similarly to a configuration that is conventionally applied in an ordinary endoscope. Accordingly, explanation of a detailed configuration and illustration of an internal configuration of the bending portion 7 is omitted. The proximal end side of the bending portion 7 is connectively provided at the distal end of the above described flexible tube portion 8, and the distal end side of the bending portion 7 is connectively provided at the proximal end of the distal end portion 6. Note that the bending portion 7 is configured so that bending in the vertical direction and the lateral direction are at will, for example, by operating a bending operation knob 9 of the operation portion 3 that will be described later.

The distal end portion 6 is a component unit that is placed at a most distal end side in a long axis direction (an insertion axis direction; refer to reference sign Ax in FIG. 2 that will be described later) of the insertion portion 4, is configured by a rigid member, and has various component members disposed on a distal end face and an inside.

The operation portion 3 is a component portion which a user grasps by hand at a time of use, and supports the endoscope 2. On an outer circumferential face of the operation portion 3, a plurality of operation members for performing various operations are placed. The plurality of operation members are respectively placed at sites within a range a hand and fingers of a user reach when the user grasps the operation portion 3. As the above described plurality of operation members, for example, an air-feeding and liquid-feeding operation button 24, a scope switch 25, a suction operation button 26, and a bending operation knob 9 are cited specifically.

Figure 3:
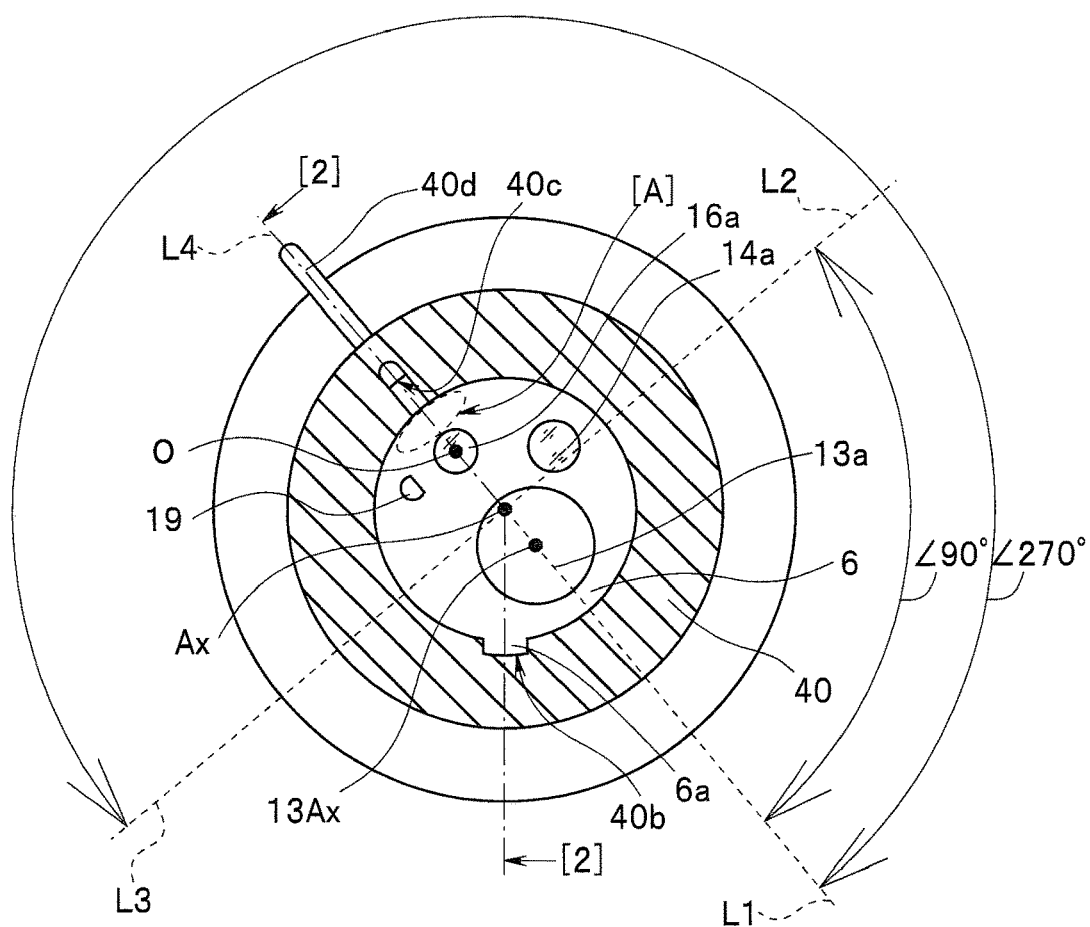
FIG. 3 is a sectional view along line [3] to [3] in FIG. 2.

The air-feeding and liquid-feeding operation button 24 is an operation member for selectively jetting gas, a liquid and the like for cleaning from an observation window nozzle 19 (Not illustrated in FIG. 1. Refer to FIG. 3 described later) provided at the distal end portion 6 of the insertion portion 4.

The suction operation button 26 is an operation member for performing a suction operation at a time of recovering mucus and the like in a body cavity to outside from a channel distal end opening 13a (Not illustrated in FIG. 1. Refer to FIG. 3 described later) provided in the distal end portion 6 of the insertion portion 4 via the above described treatment instrument channel 13.

The scope switch 25 is an operation member for switching a display mode at a time of displaying an endoscopic image acquired by an image pickup section (not illustrated in FIG. 1) provided at the distal end portion 6 of the insertion portion 4 by using the display apparatus 35. The image pickup section is a component unit including, for example, an objective optical system, and an image pickup device, and as the image pickup section itself, an image pickup section similar to an image pickup section that is conventionally applied in an ordinary endoscope is applied. Accordingly, explanation of a detailed configuration and illustration of an internal configuration about the image pickup section are omitted.

Note that though not illustrated in FIG. 1, an observation window 16a that is a part of an observation optical system configuring a part of the above described image pickup section is provided on a front face of the distal end portion 6 (refer to FIG. 3). The objective optical system, the image pickup device and the like of the observation optical system not illustrated are provided behind the observation window 16a. The image pickup cable 16 extends rearward from the image pickup section (refer to FIG. 2). Note that in FIG. 2, illustration of the image pickup section is also omitted). The image pickup cable 16 is a signal cable that transmits a control signal for controlling the above described image pickup section, an image signal that is outputted from the image pickup device and the like. The image pickup cable 16 reaches a connector 29 (details will be described later) described later by being inserted through the insertion portion 4, the operation portion 3 and the universal cord 5. Thereby, the image pickup section is electrically connected to the video processor 32 via the image pickup cable 1 and the connection cable 33.

The respective operation members such as the air-feeding and liquid-feeding operation button 24, the scope switch 25 and the suction operation button 26 described above are respectively interlocked with a plurality of operation switches corresponding to the various operation members in an inside of the operation portion 3. The plurality of operation switches are mounted on an internal main substrate (not illustrated) of the operation portion 3. The internal main substrate of the operation portion 3 is electrically connected to the video processor 32 from a signal cable (not illustrated) inserted through the universal cord 5 via a connector 29 and a connection cable 33. By the configuration, when the above described respective operation members are operated by the user, corresponding predetermined instruction signals are generated from the operation switches that are interlocked with the respective operation members. The instruction signals are transmitted to the video processor 32, and corresponding control processing is executed.

The bending operation knob 9 is a rotation operation member for operating a bending operation mechanism (not illustrated) that is placed inside the operation portion 3.

As operation members that are provided at the operation portion 3, various operation members are provided besides the examples shown as described above, but detailed explanation and illustrations of the individual operation members are omitted because the individual operation members are similar to the operation members which are conventionally used generally.

At a site to the distal end of the operation portion 3, a treatment instrument insertion port 27 is provided to protrude outward from a side part. The treatment instrument insertion port 27 communicates with the treatment instrument channel 13 (Not illustrated in FIG. 1. Refer to FIG. 2 and the like) that is inserted through and disposed in insides of the operation portion 3 and the insertion portion 4. The treatment instrument channel 13 is formed by a tubular member such as a tube that is inserted through and disposed in an inside of the insertion portion 4 from the inside of the operation portion 3 and reaches the channel distal end opening 13a (Not illustrated in FIG. 1. Refer to FIG. 3 described later) that is opened in a front face of the distal end portion 6 of the insertion portion 4. That is, the treatment instrument channel 13 is a second conduit that is provided in the insertion portion 4 and causes the treatment instrument insertion port 27 at the proximal end side and the channel distal end opening 13a at the distal end side to communicate with each other. That is, a treatment instrument (not illustrated) that is inserted into a subject from outside is inserted through the treatment instrument channel 13 that is the second conduit.

When the user performs treatment or the like using a treatment instrument not illustrated via the endoscope 2 of the endoscope system 1, a predetermined treatment instrument is inserted from the above described treatment instrument insertion port 27, and after the treatment instrument is inserted through the inside of the above described treatment instrument channel 13, a distal end portion of the above described treatment instrument is protruded forward in an insertion direction from the above described channel distal end opening 13a. Thereby, a distal end site of the treatment instrument is configured to be able to reach a desired site to be inspected in a body cavity, and to thereby be able to perform various treatments of a remedy or the like.

The universal cord 5 extends outward from a side portion of the operation portion 3. The universal cord 5 is a cable member that is formed by a plurality of signal lines (not illustrated) including the image pickup cable 16 (Not illustrated in FIG. 1. Refer to FIG. 2 described later) and a light guide cable (not illustrated), the air-feeding and liquid-feeding tube 15 (Note illustrated in FIG. 1. Refer to FIG. 2), a suction tube (not illustrated) and the like being inserted through and disposed in an inside. The connector 29 is provided at a distal end of the universal cord 5.

The above described connector 29 is provided with a fluid conduit connection pipe sleeve (not illustrated), a light guide pipe sleeve (not illustrated) that is an illuminating light supply end portion, an electric contact point portion 29a and the like. Here, an air-feeding and liquid-feeding apparatus 39 is connected to the fluid conduit connection pipe sleeve, the light source apparatus 31 is connected to the light guide pipe sleeve, and one end of the connection cable 33 is connected to the electric contact point portion 29a to be respectively detachably and attachably.

A connector 33a is provided at the other end of the above described connection cable 33, and the connector 33a is connected to the video processor 32 that is signal processing and control means.

The light source apparatus 31 is a component unit that generates an illuminating light. The light guide cable is connected to the light source apparatus 31 as described above. The light guide cable is inserted through the insides of the operation portion 3 and the insertion portion 4 after being inserted through an inside of the universal cord 5, and reaches an inside of the distal end portion 6 of the insertion portion 4. Thereby, the illuminating light emitted from the light source apparatus 31 is configured to be guided to the inside of the above described distal end portion 6 by the light guide cable, and to be irradiated forward from an illumination window 14a that is provided on the front face of the distal end portion 6.

The video processor 32 is control means that performs centralized control of the present endoscope system 1, and is signal processing means that processes various electric signals. The video processor 32 supplies a control signal for driving the image pickup section and the like, and receives instruction signals from the various operation members of the operation portion 3 and outputs corresponding control signals, for example. Further, the video processor 32 performs predetermined signal processing by receiving an image signal outputted from (the image pickup device of) the image pickup section to generate an image signal for display and generates image data for recording. Consequently, an image processing section that receives various instruction signals to perform image signal processing corresponding to various instructions to an output signal (an image signal) from the image pickup section, and a plurality of substrate units configuring electronic control circuits and the like of an operation detection section and the like that detect the instruction signals from the operation portion 3 are placed inside the video processor 32.

The display apparatus 35 is a component unit for continuously displaying endoscopic images on a display screen by receiving display image signals generated by the above described video processor 32. As the display apparatus 35, an ordinary display apparatus using a CRT (cathode ray tube (Braun tube)) or the like is applied, besides a liquid crystal display (LCD) apparatus, and organic electro-luminescence (organic EL: OEL) display apparatus, for example.

The keyboard 36 is external input equipment that is electrically connected to the video processor 32, and is for inputting an instruction to the video processor 32, and inputting various kinds of information such as patient information. Note that as the external input equipment that is connected to the video processor 32, besides the above described keyboard 36, various kinds of existing devices can be properly applied, such as a sound input apparatus, and a touch panel placed on the display screen of the display apparatus 35 besides a pointing device such as a mouse, a trackball, a joystick, or touch pad, a foot switch or the like, and a configuration in which a plurality of external input devices are included at the same time may be adopted without limiting only to one external input device.

The rack 37 is a housing and placing apparatus for temporarily placing not only the component units such as the light source apparatus 31, the video processor 32, the display apparatus 35, and the external input device (the keyboard 36 or the like) described above but also the endoscope 2 at the time of being unused by suspending the endoscope 2.

Further, the present endoscope system 1 is configured by including the recording apparatus, the cautery apparatus and the like as the other medical external equipment 38. Of the apparatuses, the recording apparatus is a component section for recording various kinds of related data other than the acquired endoscopic image data, for example, patient data. Further, the cautery apparatus is medical equipment for giving energy by a high-frequency current or the like to the treatment instrument such as an electric knife in a subject, and is specifically external medical equipment called an electric knife apparatus or the like.

Further, in the endoscope system 1 including the endoscope apparatus of the present embodiment, the endoscope apparatus is configured by the endoscope 2, the endoscope over tube 40 that is the distal end covering portion in which the endoscope 2 is inserted and disposed, and the suction apparatus 41.

In the above described endoscope apparatus, the endoscope over tube (hereinafter, simply referred to as the over tube) 40 is a distal end covering portion that allows insertion of at least the outer circumferential portion of the distal end portion of the insertion portion 4 of the endoscope 2 so as to cover the outer circumferential portion, and is held in the distal end portion 6 of the insertion portion 4. That is, the over tube 40 is the distal end covering portion, which is extended in the direction along the long axis Ax along the insertion portion 4, and through which the insertion portion 4 is inserted.

The suction apparatus 41 is an apparatus that is connected to a proximal end side of a suction conduit 40a (Not illustrated in FIG. 1. Refer to FIG. 2 and the like. Details are described later) that is the first conduit internally inserted in the above described over tube 40, and has a function of discharging a fluid or the like including gas, specifically, liquid droplets and the like in the mist state including fat, living tissue and the like to outside from a subject (body cavity) via the suction conduit 40a.

A schematic configuration of the endoscope system 1 including the endoscope apparatus of the present embodiment is as above. Components omitted in the above described explanation are assumed to have the configurations similar to the components of the endoscope system that is conventionally and generally used practically.

Next, of the detailed configuration of the endoscope apparatus in the endoscope system 1 including the endoscope apparatus of the present embodiment, a configuration of the distal end portion 6 of the insertion portion 4 in the above described endoscope 2, and a configuration of the over tube 40 that is the above described distal end covering portion are described in particular hereunder by mainly using FIG. 2 and FIG. 3. FIG. 2 is a view illustrating an outline of a section along the long axis Ax, with respect to the configuration of the endoscope apparatus of the present embodiment in a state in which the insertion portion of the above described endoscope is inserted through the above described distal end covering portion (over tube). FIG. 3 is a sectional view along line [3] to [3] in FIG. 2. Note that in FIG. 2 and FIG. 3, the internal configuration of the endoscope 2 is not directly related to the gist of the present invention, and therefore is illustrated by being simplified.

As illustrated in FIG. 2, in the endoscope system 1 including the endoscope apparatus of the present embodiment, the above described treatment instrument channel 13, the above described air-feeding and liquid-feeding tube 15, the above described image pickup cable 16 and the like are inserted through and disposed in the inside of the distal end portion 6 of the insertion portion 4 of the above described endoscope 2, from the distal end toward the proximal end side.

Further, as illustrated in FIG. 3, the above described channel distal end opening 13a, the illumination window 14a, the observation window 16a, the observation window nozzle 19 and the like are placed on the distal end face of the above described distal end portion 6.

In the endoscope 2, a protruded portion 6a is formed at a predetermined site on an outer circumferential face of the above described distal end portion 6 to be provided to protrude outward in a radial direction. As described later, the protruded portion 6a is provided to define a position of the distal end portion 6 to the over tube 40 in a rotation direction with the long axis Ax of the above described insertion portion 4 as a center, when the insertion portion 4 of the endoscope 2 is inserted through and disposed in the inside of the over tube 40 that is the distal end covering portion, and the over tube 40 is brought into a state held with respect to the above described distal end portion 6. Specifically, the above described protruded portion 6a functions as a part of a positioning portion that defines a position in which the observation window 16a in the above described distal end portion 6 in a state held in the over tube 40 should be disposed with respect to the suction conduit 40a (described later) (details will be described later).

Other configurations in the endoscope 2 are similar to configurations of the ordinary endoscope that is conventionally used widely in general.

The over tube 40 is a tubular member in a mode in which the insertion portion 4 of the above described endoscope 2 can be inserted through the inside. The over tube 40 is formed by having the suction conduit 40a, a groove portion 40b, a conduit opening 40c, a suction tube 40d, an inward flange 40e and a distal end opening 40f.

The inward flange 40e is formed at a distal end of the over tube 40, and forms the distal end opening 40f. The distal end opening 40f is formed to have a slightly smaller diameter than an outside diameter dimension of the distal end portion 6 of the insertion portion 4 of the endoscope 2, which is inserted through and disposed in the inside of the over tube 40. Accordingly, the endoscope 2 which is inserted through and disposed in the inside of the over tube 40 is configured so as not to protrude forward from the distal end opening 40f of the over tube 40.

The suction conduit 40a that is a first conduit that is inserted through the inside along the axial direction from the distal end side toward the proximal end side is formed in a tubular portion of the above described over tube 40. A distal end side of the suction conduit 40a is connected to the conduit opening 40c that opens toward an inner surface side of the above described inward flange 40e.

The conduit opening 40c is provided by being bored in one site of an inner face (an inner surface) of the above described inward flange 40e in a site to which an outer circumferential edge portion of the distal end face of the above described distal end portion 6 is adjacent when the endoscope 2 is inserted through and disposed in the inside of the above described over tube 40. Thereby, the conduit opening 40c is an opening portion at a distal end side of the above described suction conduit 40a.

One end of the suction tube 40d is connected to a proximal end side of the above described conduit opening 40c. The other end of the suction tube 40d is connected to the suction apparatus 41. By the configuration, the suction conduit 40a and the suction tube 40d have a function of discharging a fluid (liquid droplets and the like in a mist state including fat, living tissue and the like) including gas to outside of the subject from the inside of the subject via the conduit opening 40c which is disposed adjacently to the distal end face of the insertion portion 4 by a suction action of the above described suction apparatus 41.

The groove portion 40b is a recessed groove portion that is formed substantially parallel with the long axis Ax from a distal end to a proximal end in an inner circumferential face of the above described over tube 40. The above described groove portion 40b is a site in which the above described protruded portion 6a in the above described endoscope 2 is fitted and disposed when the endoscope 2 is inserted through and disposed in the over tube 40. That is, the endoscope 2 is configured to be able to be inserted through the inside of the over tube 40 along the long axis Ax, only when the protruded portion 6a of the endoscope 2 is brought into a state fitted in the groove portion 40b of the over tube 40. By the configuration like this, the endoscope 2 in the state inserted through and disposed in the inside of the over tube 40 is brought into a state in which a position is restricted in the rotation direction with the long axis Ax as the center. Accordingly, here, the groove portion 40b functions as a positioning portion that defines a position of the conduit opening 40c of the suction conduit 40a in the rotation direction with the long axis Ax of the insertion portion 4 as the center, when the over tube 40 (the distal end covering portion) is held by the distal end portion 6, with the above described protruded portion 6a.

Note that as described above, the conduit opening 40c is configured to be disposed in a vicinity of the observation window 16a, that is a site to which the outer circumferential edge portion of the distal end face of the above described distal end portion 6 is adjacent, when the endoscope 2 is inserted through and disposed in the inside of the over tube 40.

In this case, the conduit opening 40c is desirably provided to be located in a region that faces to a second straight line L2 or L3, when a first straight line (a dotted-line straight line denoted by reference sign L1 in FIG. 3) connecting an optical axis O of the observation window 16a which is a part of the observation optical system and the above described channel distal end opening 13a which is provided on the distal end face of the above described distal end portion 6, and a second straight line (reference sign L2 or reference sign L3 in FIG. 3) that passes through a median point between the optical axis O of the observation window 16a and a center axis (reference sign 13Ax in FIG. 3) of the channel distal end opening 13a to be orthogonal to the first straight line L1 are defined. In other words, the conduit opening 40c is desirably placed at an opposite side to a placement position of the above described channel distal end opening 13a with the long axis Ax (a center point of the distal end face (refer to FIG. 3)) between the conduit opening 40c and the channel distal end opening 13a.

In general, the above described channel distal end opening 13a is disposed in a region to a lower side in the distal end face of the above described distal end portion 6 in the endoscope 2. Therefore, the above described conduit opening 40c is desirably disposed in a site adjacent to the outer circumferential edge portion to an upper side of the distal end face of the above described distal end portion 6.

As disposition of the above described conduit opening 40c, more specifically, the disposition is desirably made in an upper region from the channel distal end opening 13a, in the distal end face of the distal end portion 6 in the endoscope 2, for example. Here, the conduit opening 40c is desirably disposed in the vicinity of the observation window 16a as described above, but does not have to be adjacent most closely to the observation window 16a, and can be disposed properly in a predetermined site.

In other words, as the positioning portion, the protruded portion 6a and the groove portion 40b position the conduit opening 40c so that the conduit opening 40c of the suction conduit 40a is located in a region within a range from the straight line (reference sign L2 in FIG. 3) which is rotated by an angle of 90 degrees to the straight line (reference sign L3 in FIG. 3) that is rotated by an angle of 270 degrees inclusive with respect to the straight line (the dotted straight line denoted by reference sign L1 in FIG. 3) which connects the optical axis O of the observation window 16a and the center axis (reference sign 13Ax in FIG. 3) of the treatment instrument channel 13 that is a second conduit, in an orthogonal direction.

Like this, according to the configuration in which the conduit opening 40c is disposed in the upper region in the distal end face, a liquid and the like that stay in the body cavity are not sucked simultaneously when the liquid droplets and the like in the mist state that float in the body cavity are sucked, which is highly convenient. It is possible to suck the liquid and the like which are staying to outside by the suction action by the conventional suction function from the above described channel distal end opening 13a that is provided in the lower region, in the distal end face of the distal end portion 6 in the endoscope 2.

Note that a case is also conceivable, in which the long axis Ax that is the center axis of the insertion portion 4 passes through the median point between the optical axis O of the observation window 16a and the channel distal end opening 13a in the first straight line (reference sign L1 in FIG. 3) connecting the optical axis O of the observation window 16a and the center axis (reference sign 13Ax in FIG. 3) of the above described channel distal end opening 13a provided in the distal end face of the above described distal end portion 6.

At the time, the conduit opening 40c is positioned so as to be located in the region that faces the channel distal end opening 13a with respect to the long axis Ax (the center point of the distal end face (refer to FIG. 3)) of the insertion portion 4.

Further in other words, the configuration is as follows. That is, the protruded portion 6a and the groove portion 40b as the positioning portion position themselves (the positioning portion; the protruded portion 6a and the groove portion 40b) within a range from a straight line (approximated to reference sign L3 in FIG. 3) rotated by the angle of 90 degrees to a straight line (approximated to reference sign L2 in FIG. 3) rotated by the angle of 270 degrees inclusive, with respect to a straight line (reference sign L4 in FIG. 3) that connects, in an orthogonal direction, the optical axis O of the observation window 16a that is a part of the observation optical system and the center axis (reference sign 13Ax in FIG. 3) of the treatment instrument channel 13 that is the second conduit, and position the conduit opening 40c on a side facing the positioning portion with the long axis Ax between the positioning portion and the conduit opening 40c.

In the case like this, at a time of sucking liquid droplets and the like in a mist state that float in the body cavity, the liquid and the like that stay in the body cavity can be prevented from being sucked at the same time.

Note that here as a distinction between the upper part and the lower part, the upper and the lower part correspond to an upper part and a lower part in the screen of an endoscopic image that is acquired by (the image pickup section) of the endoscope 2.

Here, a positional relationship between the above described protruded portion 6a and the groove portion 40b is restricted so that when the endoscope 2 is inserted through and disposed in the inside of the over tube 40, the conduit opening 40c of the over tube 40 is disposed in the vicinity of the observation window 16a on the distal end face of the distal end portion 6 in the endoscope 2 (refer to FIG. 3).

In the endoscope system 1 including the endoscope apparatus of the present embodiment configured in this way, the endoscope 2 is inserted through and disposed in the inside of the over tube 40. At the time, the protruded portion 6a of the above described distal end portion 6 is fitted in the groove portion 40b of the over tube 40, and the above described distal end portion 6 is inserted along the groove portion 40b. Subsequently, the above described distal end portion 6 is disposed in a predetermined position in which the distal end face of the distal end portion 6 substantially abuts on the inner face of the inward flange 40e at the distal end of the above described over tube 40 (refer to FIG. 2). At the time, the conduit opening 40c of the over tube 40 is disposed in the vicinity of the observation window 16a on the distal end face of the distal end portion 6 (refer to FIG. 3).

It is assumed that when the endoscope 2 which is inserted through and disposed in the inside of the over tube 40 in this way is used in a body cavity, for example, a procedure of treatment or the like by ESD or the like is implemented to a desired treatment target site in the body cavity by a treatment instrument that is inserted through the treatment instrument insertion channel, for example, and is provided to protrude to a front face from the above described channel distal end opening 13a.

Note that here, the procedure of treatment or the like by ESD or the like is performed by using the endoscope inserted into the subject, for example. In this case, treatment of performing cautery or the like of a part of the subject by giving energy to the treatment instrument inserted through the treatment instrument channel in the endoscope in the subject is involved. For the purpose, the endoscope system 1 including the endoscope apparatus of the present embodiment is configured by including a cautery apparatus (refer to reference sign 38 in FIG. 1) for giving energy to the treatment instrument in the subject. To the cautery apparatus itself, an apparatus that is conventionally used widely in general can be applied, and therefore, detailed explanation of the cautery apparatus is omitted.

By applying the treatment like this, the liquid droplets and the like in the mist state including fat, living tissue and the like are vaporized from the treatment target site. Thereupon, in this case, the suction apparatus 41 is automatically operated in synchronism with timing of implementation of the above described treatment in the endoscope system 1. Alternatively, the suction apparatus 41 may be operated manually by a user.

Then, the liquid droplets and the like in the mist state including fat, living tissue and the like which are vaporized into the above described body cavity are drawn out (discharged) to outside from the above described conduit opening 40c via the suction conduit 40a and the suction tube 40d by an action of the suction apparatus 41.

In other words, the above described suction apparatus 41 discharges mist that is the liquid droplets and the like in a mist state including fat, living tissue and the like that are generated at the time of the above described cautery apparatus (refer to reference sign 38 in FIG. 1) cauterizing a part of the subject to outside of the subject from the inside of the subject via the above described suction conduit 40a.

Further, when air feeding and liquid feeding are performed from the observation window nozzle 19 at the time, cleaning gas, liquid and the like that stay in a region (refer to a region denoted by reference sign [A] in FIG. 3) between the conduit opening 40c and the observation window 16a are also sucked to the conduit opening 40c, in the distal end face of the distal end portion 6.

Furthermore, a suction operation using the suction operation button 26 or the like included in the endoscope 2 is simultaneously performed, whereby a fluid and the like staying in the over tube 40 can be also sucked from the channel distal end opening 13a.

By the actions, the liquid droplets and the like in the mist state including fat, living tissue and the like floating in the vicinity of the observation window 16a, cleaning gas, a liquid and the like are removed. Accordingly, the endoscopic image that is obtained by the image pickup section that is behind the observation window 16a and is provided inside the above described distal end portion 6 is always a clear image.

As described above, according to the above described first embodiment, the endoscope system 1 is configured by including the endoscope 2 having the distal end portion 6 at the distal end of the insertion portion 4 that is inserted into a subject, the over tube 40 that is the distal end covering portion that covers at least the outer periphery of the distal end portion 6 of the insertion portion 4 and includes the suction conduit 40a that is held by the insertion portion 4 and internally inserted through a space from the conduit opening 40c at the distal end side to the suction tube 40d connected to the proximal end side in order to discharge a fluid and the like including gas to outside of the subject from the inside of the subject, and the suction apparatus 41 that is connected via the suction tube 40d that is connected to the proximal end side of the above described suction conduit 40a.

In this case, the conduit opening 40c at the distal end side of the above described suction conduit 40a is disposed at the position adjacent to the distal end face of the distal end portion 6 of the insertion portion 4. Further, the protruded portion 6a is provided on the outer circumferential face in the distal end portion 6 of the endoscope 2, and the groove portion 40b is provided on the inner circumferential face of the over tube 40 correspondingly to the protruded portion 6a.

By the configuration as above, when the over tube 40 (the distal end covering portion) is held by the distal end portion 6 of the insertion portion 4 of the endoscope 2, the position of the suction conduit 40a in the rotation direction with the long axis Ax of the insertion portion 4 as the center is defined by the protruded portion 6a and the groove portion 40b that configure the positioning portion.

Accordingly, when treatment or the like such as ESD is performed by using the endoscope system 1 including the endoscope apparatus of the present embodiment, the liquid droplets and the like in the mist state including fat, living tissue and the like generated in the body cavity can be reliably sucked to outside by properly operating the suction apparatus 41 at predetermined timing during implementation of the procedure, whereby a clear endoscopic image can be always acquired.

Note that in the above described first embodiment, the protruded portion 6a which is provided as the positioning portion in the distal end portion 6 is illustrated in the mode in which the protruded portion 6a is configured integrally with the distal end portion 6 on the outer circumferential face of the distal end portion 6. However, as for the protruded portion 6a as the above described positioning portion, various other modes are conceivable without being limited to the mode.

Figure 4:
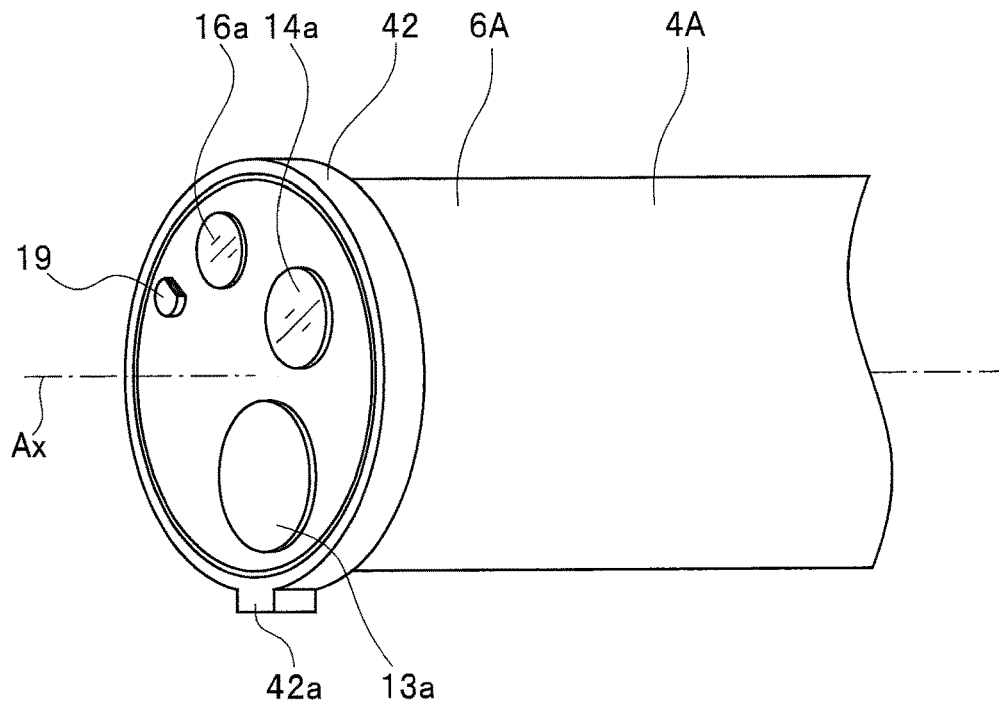
FIG. 4 is a schematic perspective view showing a vicinity of an endoscope distal end portion of one modification of the first embodiment of the present invention.
Figure 5:
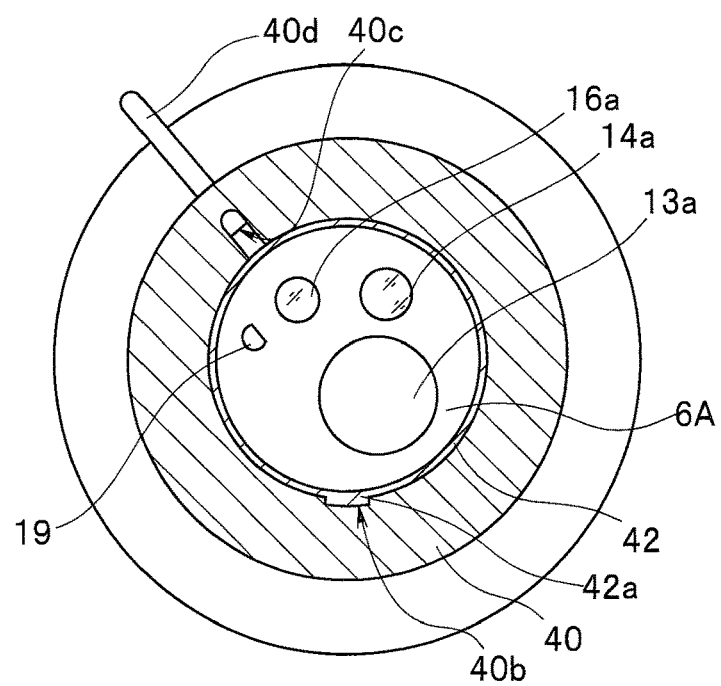
FIG. 5 is a sectional view in the endoscope distal end portion shown in FIG. 4 (a sectional view of a site corresponding to line [3] to [3] in FIG. 2)

For example, FIG. 4 and FIG. 5 are views illustrating one modification of the endoscope in the endoscope system including the endoscope apparatus of the above described first embodiment. Of FIG. 4 and FIG. 5, FIG. 4 is a schematic perspective view of the vicinity of the endoscope distal end portion. FIG. 5 is a view illustrating a section of the distal end covering portion (over tube) in the state in which the endoscope is inserted through and disposed in the distal end covering portion. Note that FIG. 5 is a section of a site corresponding to line [3] to [3] in FIG. 2.

In the illustration of the above described one modification, an annular member 42 in a shape capable of being fitted and disposed on a distal end portion of an insertion portion 4A of an endoscope in an ordinary shape is provided as a separate body. The annular member 42 is formed by having a protruded portion 42a in a totally same mode in the above described first embodiment, at a predetermined site on an outer circumferential face of the annular member 42. The annular member 42 may be formed attachably to and detachably from a distal end portion 6A of the endoscope 2, or may be fixed to the distal end portion 6A of the endoscope 2 by means of bonding or the like. The other configurations are totally similar to the configurations in the aforementioned first embodiment.

According to the above described one modification configured in this way, a totally similar effect to the effect of the aforementioned first embodiment can be obtained. Further, according to the present modification, the above described annular member 42 is only prepared, whereby the conventional endoscope can be easily incorporated into the endoscope system like the above described first embodiment. That is, the above described annular member 42 is only attached to the distal end portion of the endoscope in the conventional mode, whereby the annular member 42 can be caused to correspond to the over tube 40 (the distal end covering portion) described in the above described first embodiment.

Further, in the aforementioned first embodiment and the above described one modification, the modes in which the protruded portions (6a, 42a) are provided at the distal end portion sides of the endoscopes, and the groove portions 40b are provided at the distal end covering portion sides (the over tube 40 sides) are illustrated, but the present invention is not limited to the example. For example, a mode may be adopted, in which a recessed groove is provided at the distal end portion side, and a protruded portion is provided at the distal end covering portion side (the over tube 40 side).

In the aforementioned first embodiment, as the distal end covering portion, the over tube 40 is applied, which is configured to cover the insertion portion 4 of the endoscope 2. However, as for the specific mode of the above described distal end covering portion, it is also possible to configure the distal end covering portion in another mode, without being limited to the aforementioned mode. That is, in the configuration of the present invention, the distal end covering portion can be any distal end covering portion in a mode in which the distal end covering portion covers at least the outer circumferential portion of the distal end portion 6 of the insertion portion 4 in the endoscope 2, and is held by the distal end portion 6. A second embodiment that will be described next illustrates a different mode of the distal end covering portion.

Second Embodiment

Figure 6:
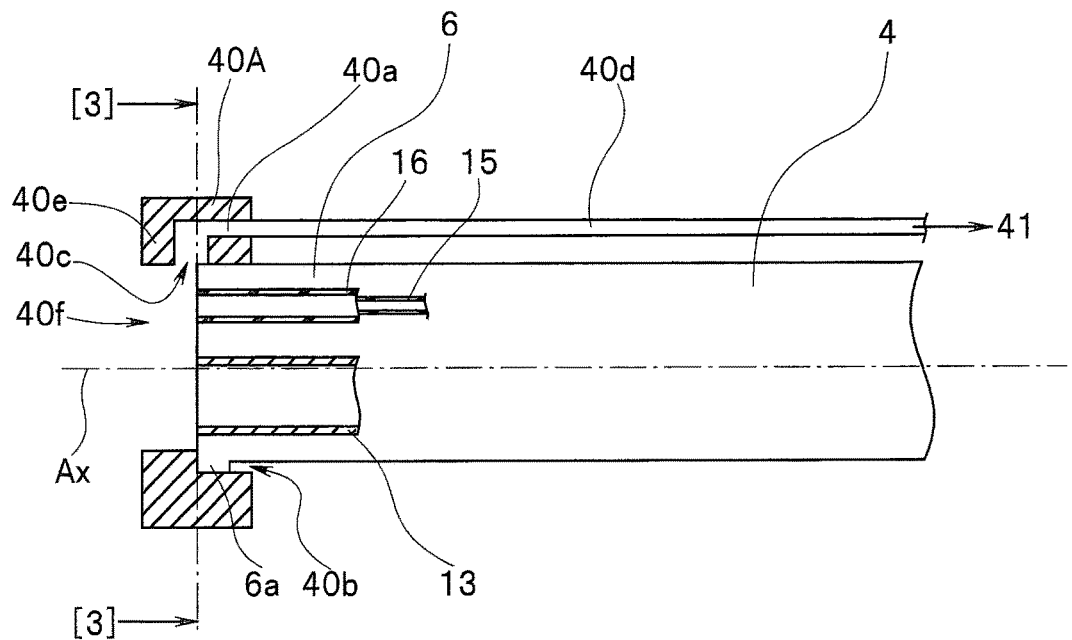
FIG. 6 is a vertical sectional view showing a part of a configuration of an endoscope apparatus of a second embodiment of the present invention.

FIG. 6 is a view illustrating a part of a configuration of an endoscope apparatus of a second embodiment of the present invention. In detail, FIG. 6 is a vertical sectional view of an endoscope distal end portion and a distal end covering portion in the endoscope apparatus of the present embodiment. In FIG. 6, a section along an insertion axis (the long axis Ax) of an endoscope is illustrated.

A basic configuration of the present embodiment is substantially similar to the aforementioned first embodiment, and differs only in a mode of the distal end covering portion. Specifically, in the aforementioned first embodiment, the over tube 40 configured to cover the outer face of the insertion portion of the endoscope is illustrated as the distal end covering portion. In the present embodiment, an endoscope distal end hood 40A is illustrated as the mode of the distal end covering portion that covers an outer periphery of the distal end portion 6 of the insertion portion 4 of the endoscope 2 and is held by the distal end portion 6. The other configurations are substantially similar to the configurations of the aforementioned first embodiment. Accordingly, in the following explanation, component portions similar to the component portions of the aforementioned first embodiment are assigned with the same reference signs and explanation of the similar component portions is omitted.

As described above, the endoscope distal end hood 40A that is the distal end covering portion in the present embodiment is placed to cover the outer periphery of the distal end side of the distal end portion 6 of the insertion portion 4 of the endoscope 2, as illustrated in FIG. 6, and is held by the distal end portion 6.

The endoscope distal end hood 40A is a distal end covering portion that is configured by a member in a substantially annular shape as a whole, and is fitted to a site near to a distal end of the distal end portion 6 of the insertion portion 4 of the above described endoscope 2. The endoscope distal end hood 40A is formed by having the suction conduit 40a, the groove portion 40b, the conduit opening 40c, the suction tube 40d, the inward flange 40e, and the distal end opening 40f similarly to the over tube 40 of the aforementioned first embodiment. The inward flange 40e is formed at a distal end of the endoscope distal end hood 40A and forms the distal end opening 40f.

The suction conduit 40a that is an insertion path is formed in an inside of the above described endoscope distal end hood 40A. A distal end side of the suction conduit 40a is connected to the conduit opening 40c that is opened to an inner face side of the above described inward flange 40e. Further, the suction tube 40d is connected to a proximal end side of the above described suction conduit 40a. The suction apparatus 41 is connected to the other end of the suction tube 40d.

The above described conduit opening 40c is provided by being bored in one site of an inner face (inner surface) of the above described inward flange 40e, that is a site to which the outer circumferential edge portion of the distal end face of the distal end portion 6 is adjacent, when the above described endoscope distal end hood 40A is fitted onto the above described distal end portion 6. The conduit opening 40c is an opening portion at the distal end side of the above described suction conduit 40a.

Further, on an inner circumferential face of the above described endoscope distal end hood 40A, the groove portion 40b is formed substantially parallel with the long axis Ax. The groove portion 40b is a site in which the protruded portion 6a of the distal end portion 6 is fitted and disposed when the endoscope distal end hood 40A is fitted to the distal end portion 6 of the endoscope 2. By the configuration, the endoscope 2 which has the endoscope distal end hood 40A fitted onto the distal end portion 6 is brought into a state in which the endoscope 2 has a position restricted in the rotation direction with the long axis Ax as the center. In this state, the conduit opening 40c is configured to be disposed in the vicinity of the observation window 16a. The other configurations are substantially similar to the configurations of the above described first embodiment.

In the endoscope system 1 including the endoscope apparatus of the present embodiment configured in this way, the endoscope distal end hood 40A is fitted onto the distal end portion 6 of the endoscope 2. At the time, the above described distal end portion 6 is disposed in a predetermined position in which the distal end face of the distal end portion 6 substantially abuts on the inner face of the inward flange 40e at the distal end of the endoscope distal end hood 40A, while a state in which the protruded portion 6a of the above described distal end portion 6 is fitted into the groove portion 40b of the endoscope distal end hood 40A is kept (refer FIG. 6). At the time, the conduit opening 40c of the endoscope distal end hood 40A is disposed in the vicinity of the observation window 16a in the distal end face of the distal end portion 6. The following operations are similar to the operations in the aforementioned first embodiment.

As described above, according to the above described second embodiment, a similar effect to the effect of the aforementioned first embodiment can be obtained. Further, according to the configuration of the present embodiment, as the mode of the distal end covering portion, the endoscope distal end hood 40A in the mode in which the endoscope distal end hood 40A covers a part of the outer periphery of the distal end portion 6 is adopted, so that the mode is not a mode in which the distal end covering portion covers the outer faces of the bending portion 7 and the like of the insertion portion 4 of the endoscope 2. Accordingly, a bending operation of the endoscope 2 is not inhibited.

Note that in the present embodiment, the mode of the one modification in the aforementioned first embodiment also can be applied totally similarly. Further, in the present embodiment, a mode of placement of the protruded portion at the distal end portion side and the groove portion at the endoscope distal end hood side may be made a mode in which the protruded portion and the groove portion are exchanged respectively, that is, a mode in which the recessed groove is provided in the distal end portion side, and the protruded portion is provided at the distal end covering portion side (the endoscope distal end hood 40A side), for example.

Third Embodiment

Figure 7:
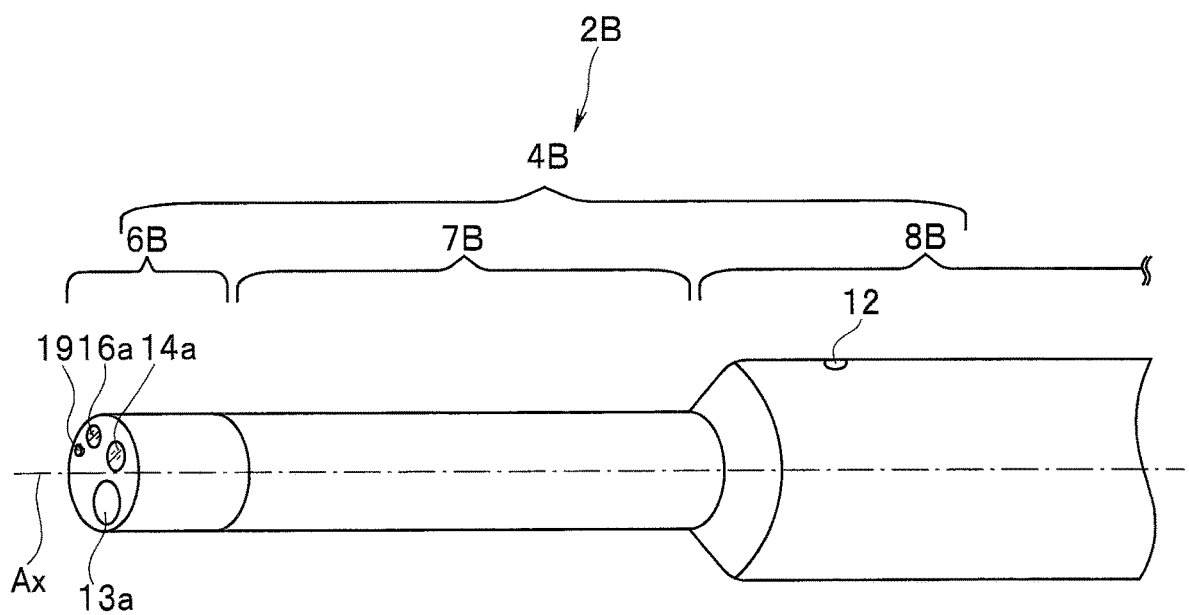
FIG. 7 is an essential part schematic perspective view showing a part of a distal end side of an endoscope in an endoscope apparatus of a third embodiment of the present invention.
Figure 8:
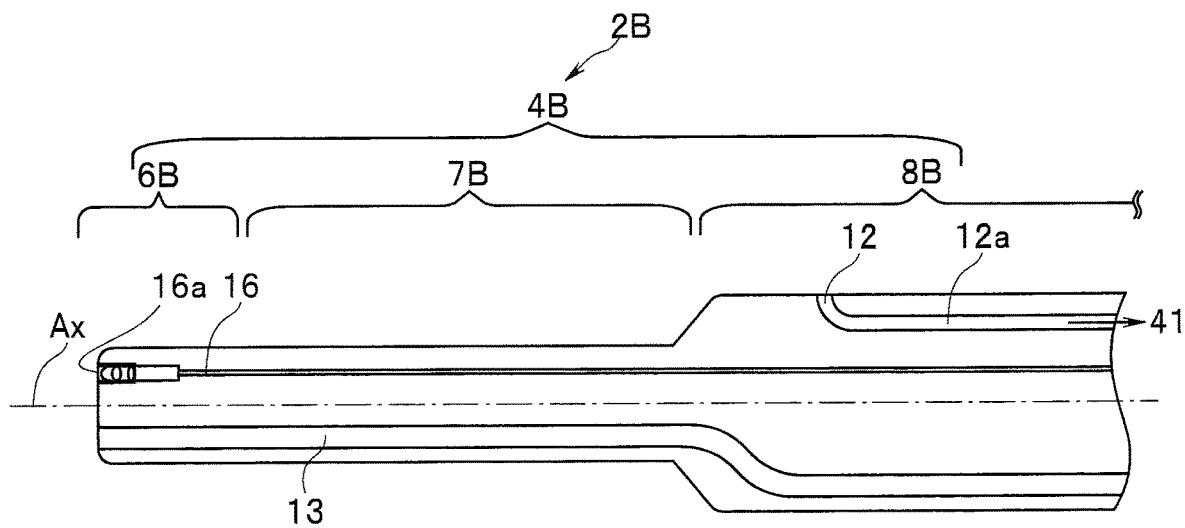
FIG. 8 is a schematic sectional view showing a section along a long axis of the endoscope in FIG. 7.
Figure 9:
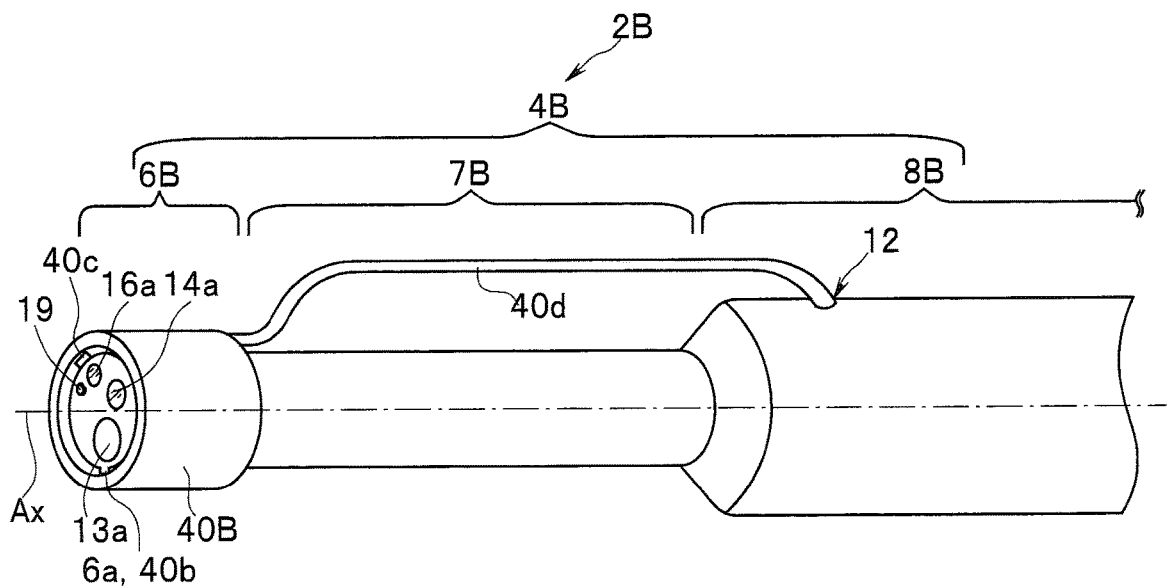
FIG. 9 is an essential part schematic perspective view showing a part of a distal end side of the endoscope apparatus in FIG. 7.

FIG. 7 to FIG. 9 are views illustrating a third embodiment of the present invention. Of FIG. 7 to FIG. 9, FIG. 7 is an essential part schematic perspective view illustrating a part of a distal end side of an endoscope in an endoscope apparatus of the present embodiment. FIG. 8 is a schematic sectional view illustrating a section along a long axis of the endoscope in FIG. 7. FIG. 9 is an essential part schematic perspective view illustrating a part of a distal end side of the endoscope apparatus of the present embodiment. In FIG. 9, a state in which an endoscope distal end hood is fitted on the endoscope is illustrated.

A basic configuration of the present embodiment is substantially similar to the aforementioned second embodiment, and is an illustration of the mode using the endoscope distal end hood as the distal end covering portion. In the present embodiment, a mode of the endoscope to which the endoscope distal end hood is applied slightly differs. Accordingly, in the following explanation, component portions similar to the component portions of the aforementioned second embodiment are assigned with the same reference signs and explanation of the similar component portions is omitted.

An endoscope 2B in the endoscope apparatus of the present embodiment is configured by an operation portion, an insertion portion 4B, a universal cord and the like in the basic configuration, similarly to the above described respective embodiments. The above described insertion portion 4B is a component unit in an elongated tube shape formed by a distal end portion 6B, a bending portion 7B and a flexible tube portion 8B being connectively provided in sequence from a distal end.

Here, in the endoscope 2B of the present embodiment, as illustrated in FIG. 7, an outside diameter of the flexible tube portion 8B is configured to be slightly larger as compared with outside diameters of the distal end portion 6B and the bending portion 7B. An endoscope side suction conduit opening 12 is provided by being bored on a site nearer to a proximal end than the bending portion 7B, for example, on an outer circumferential face near to a distal end of the flexible tube portion 8B as illustrated in FIG. 7 and the like in the present embodiment. To the endoscope side suction conduit opening 12, one end of a distal end side of an endoscope side suction conduit 12a (refer to FIG. 8) that is inserted through an inside of the flexible tube portion 8B of the endoscope 2B is connected. Note that the other end at a proximal end side of the endoscope side suction conduit 12a is connected to the suction apparatus 41 (refer to FIG. 8).

Note that on a distal end face of the distal end portion 6B of the insertion portion 4B of the endoscope 2B, the channel distal end opening 13a, the illumination window 14a, the observation window 16a, the observation window nozzle 19 and the like are placed similarly to the aforementioned respective embodiments. Further, the protruded portion 6a (not illustrated) is provided on the outer circumferential face near to the distal end of the distal end portion 6B. Note that, a configuration in which a protruded portion is included by using the annular member 42 shown in the one modification of the aforementioned first embodiment instead of providing the protruded portion 6a can be adopted.

The endoscope distal end hood 40B which is the distal end covering portion in the endoscope apparatus of the present embodiment is substantially similar to the endoscope distal end hood 40A of the above described second embodiment in the basic configuration. That is, the endoscope distal end hood 40B is similar to the endoscope distal end hood 40A of the above described second embodiment, in a point that the endoscope distal end hood 40B is configured by having a suction conduit (not illustrated), the conduit opening 40c and the groove portion 40b in a substantially similar mode to the endoscope distal end hood 40A of the above described second embodiment, and the suction tube 40d, the inward flange, the distal end opening and the like.

The present embodiment differs from the above described second embodiment in a point that in the present embodiment, the suction tube 40d which is extending rearward of the endoscope distal end hood 40B is connected to the endoscope side suction conduit 12a via the endoscope side suction conduit opening 12 of the above described endoscope 2B as illustrated in FIG. 9. The endoscope side suction conduit 12a is a conduit of a different system from a fluid conduit (not illustrated) for suction that is conventionally applied in the endoscope of a general configuration, and is specifically provided as a conduit for sucking liquid droplets and the like in a mist state including fat, living tissue and the like.

That is, the suction conduit in the endoscope apparatus of the present embodiment is formed by the endoscope side suction conduit 12a that is inserted through the inside of the insertion portion 4B at the proximal end side of the insertion portion 4B, the suction tube 40d that is exposed on an outside of the insertion portion 4B at the distal end side of the insertion portion 4B, and the suction conduit 40a that is inserted through the endoscope distal end hood 40B (the distal end covering portion) communicating with one another, and has a mode in which the endoscope distal end hood 40B (the distal end covering portion) holds the conduit opening 40c which is the opening portion provided at the distal end of the above described suction conduit 40a. The other configurations are substantially similar to the configurations of the above described second embodiment.

In the endoscope system including the endoscope apparatus of the above described third embodiment configured in this way, a substantially similar operation to the operation of the above described second embodiment is performed, and thereby a substantially similar effect can be obtained.

Further, according to the configuration of the present embodiment, the endoscope side suction conduit opening 12 which connects to the endoscope side suction conduit 12a which is inserted through the inside of the insertion portion 4B is provided in the site at the proximal end side from the bending portion 7B of the insertion portion 4B of the endoscope 2B, and the suction tube 40d which is extended from the endoscope distal end hood 40B which is the distal end covering portion is configured to be connected to the endoscope side suction conduit opening 12.

By the configuration, in the present embodiment, the endoscope side suction conduit 12a is provided inside the endoscope, so that the tube or the like which is exposed outside can be restricted to be minimum, whereby insertion and removal of the endoscope can be performed without hindrance by similar operability to the endoscope in the conventional mode.

Further, in the present embodiment, the endoscope side suction conduit opening 12 is provided in the site nearer to the proximal end than the bending portion 7B, and the endoscope side suction conduit 12a is configured to be inserted through the inside of the insertion portion 4B which is nearer to the proximal end than the endoscope side suction conduit opening 12, so that the outside diameter at the distal end side from the bending portion 7B can be reduced, and a degree of freedom of a bending operation of the bending portion 7B can be increased.

Note that in the present embodiment, a mode of placement of the protruded portion at the distal end portion side and the groove portion at the endoscope distal end hood side may be made a mode in which the protruded portion and the groove portion are exchanged respectively, that is, a mode in which the recessed groove is provided at the distal end portion side, and the protruded portion is provided at the distal end covering portion side (the endoscope distal end hood side).

Fourth Embodiment

Figure 10:
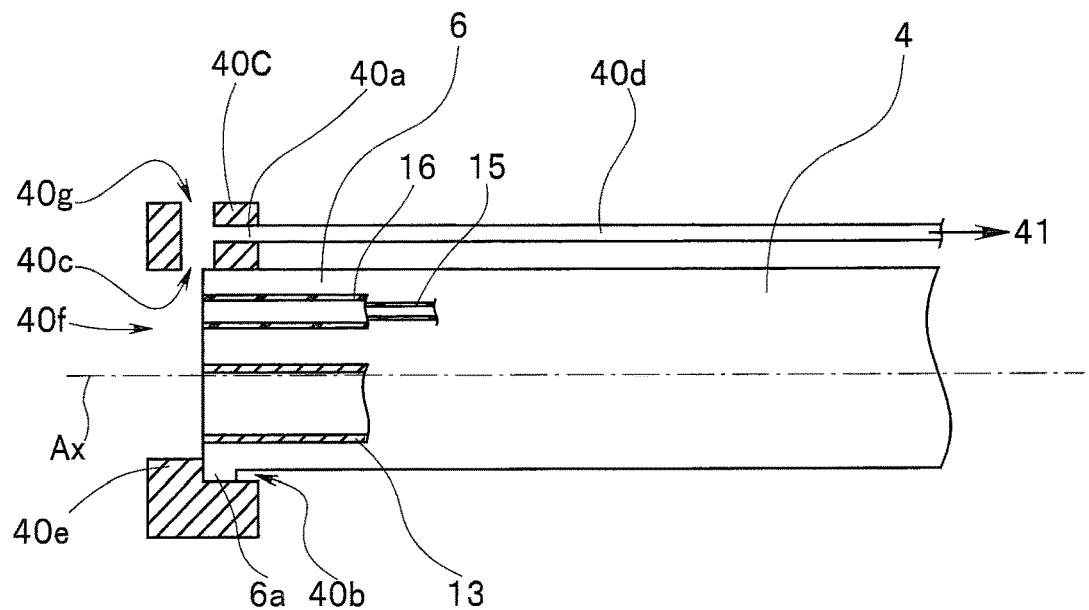
FIG. 10 is a schematic sectional view showing a section along a long axis in a distal end side in an endoscope apparatus of a fourth embodiment of the present invention.

FIG. 10 is a schematic sectional view illustrating a section along a long axis in a distal end side in an endoscope apparatus of a fourth embodiment of the present invention. In FIG. 10, a state in which an endoscope distal end hood is fitted onto an endoscope is illustrated.

A basic configuration of the present embodiment is substantially similar to the aforementioned second embodiment, and is an illustration of the mode using the endoscope distal end hood as the distal end covering portion. In the present embodiment, a mode of the endoscope distal end hood slightly differs. Accordingly, in the following explanation, component portions similar to the component portions of the aforementioned second embodiment are assigned with the same reference signs and explanation of the similar component portions is omitted.

The basic configuration of the endoscope in the endoscope apparatus of the present embodiment is similar to the basic configuration of the above described second embodiment (refer to FIG. 6).

An endoscope distal end hood 40C is a distal end covering portion that is fitted onto the distal end portion 6 of the insertion portion 4 of the above described endoscope, and is held by the distal end portion 6. A basic configuration of the endoscope distal end hood 40C is substantially similar to the basic configuration of the above described second embodiment, but differs from the basic configuration of the above described second embodiment in the following point. That is, as illustrated in FIG. 10, at a distal end side of the suction conduit 40a of the endoscope distal end hood 40C that is the distal end covering portion that is applied in the endoscope apparatus of the present embodiment, a second conduit opening 40g is provided, besides the conduit opening 40c in the same mode as in the above described second embodiment.

As described in explanation of the aforementioned second embodiment and the like, the conduit opening 40c is provided by being bored in one site on the inner face (the inner surface) of the inward flange 40e, which is the site to which the outer circumferential edge portion of the distal end face of the distal end portion 6 is adjacent when the endoscope distal end hood 40C is fitted onto the distal end portion 6, and is the opening portion at the distal end side of the suction conduit 40a.

The above described second conduit opening 40g is provided toward the outer circumferential side in the distal end side of the suction conduit 40a, that is, toward the outer surface of the endoscope distal end hood 40C, and communicates with the above described conduit opening 40c to be connected to the suction conduit 40a. That is, the above described conduit opening 40c is a distal end opening portion of the suction conduit 40a, that is provided toward inside, whereas the above described second conduit opening 40g is the second distal end opening portion of the suction conduit 40a provided toward outside. The other configurations are substantially similar to the configurations of the above described second embodiment.

In the endoscope system including the endoscope apparatus of the above described fourth embodiment configured in this way, an operation substantially similar to the operation of the above described second embodiment is performed, and thereby a substantially similar effect can be obtained.

Further, according to the configuration of the present embodiment, in the endoscope distal end hood 40C as the distal end covering portion, the second conduit opening 40g directed outward is provided in addition to the conduit opening 40c directed inward, so that suction from the outer circumferential side of the endoscope distal end hood 40C that is the distal end covering portion also becomes possible. Accordingly, a larger amount of the liquid droplets and the like in the mist state which float in the body cavity can be sucked reliably in a short time period.

Furthermore, when suction is performed with only the conduit opening 40c directed inward, the liquid droplets and the like in the mist state which are sucked sometimes pass in front or a vicinity of front face structures of the distal end portion 6, such as the observation window 16a and the like. In this regard, by the configuration in which the second conduit opening 40g which is directed outside is added, suction can be performed from outside, so that the liquid droplets and the like in the mist state which float in the body cavity can be prevented from passing in front and the vicinity of the observation window 16a and the like. Accordingly, a clear endoscopic image can be always acquired by the above.

Note that a mode in which a protruded portion is included by using the annular member 42 shown in the one modification of the aforementioned first embodiment instead of providing the protruded portion 6a at the distal end portion 6 may be adopted.

Further, in the present embodiment, a mode of placement of the protruded portion at the distal end portion side and the groove portion at the endoscope distal end hood side may be made a mode in which the protruded portion and the groove portion are exchanged respectively, that is, a mode in which the recessed groove is provided at the distal end portion side, and the protruded portion is provided at the distal end covering portion side (the endoscope distal end hood side).

Furthermore, a structure of the endoscope distal end hood of the present embodiment can be easily applied directly to the over tube or the like that is the distal end covering portion of the above described first embodiment.

Fifth Embodiment

Figure 11:
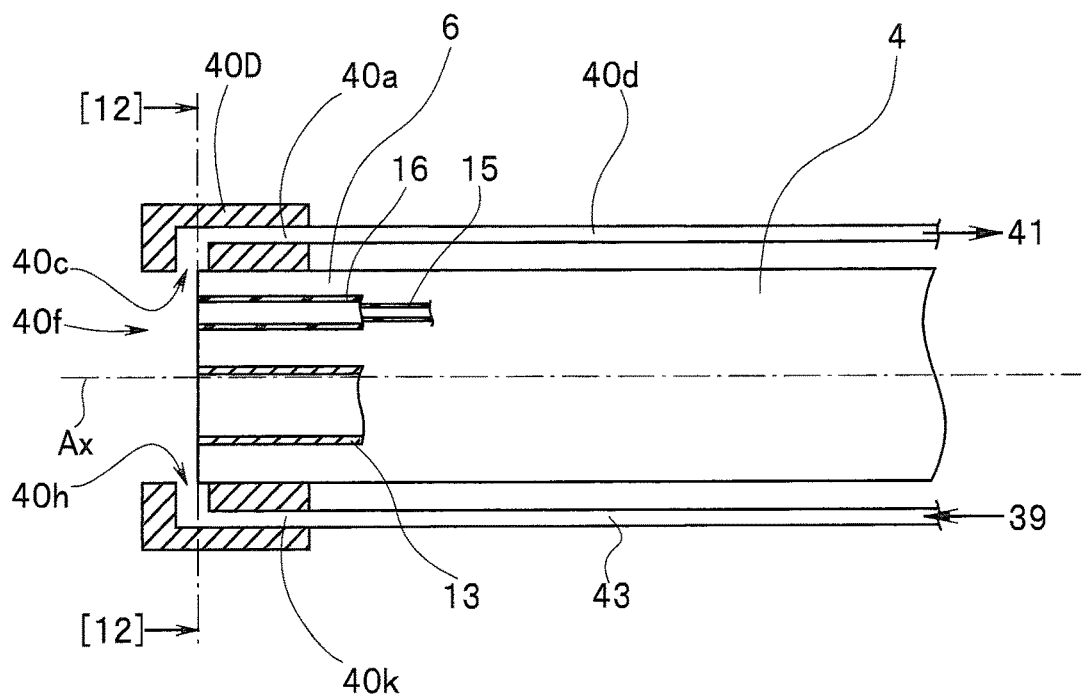
FIG. 11 is a schematic sectional view showing a part of a distal end side of an endoscope apparatus of a fifth embodiment of the present invention in a section along a long axis.
Figure 12:
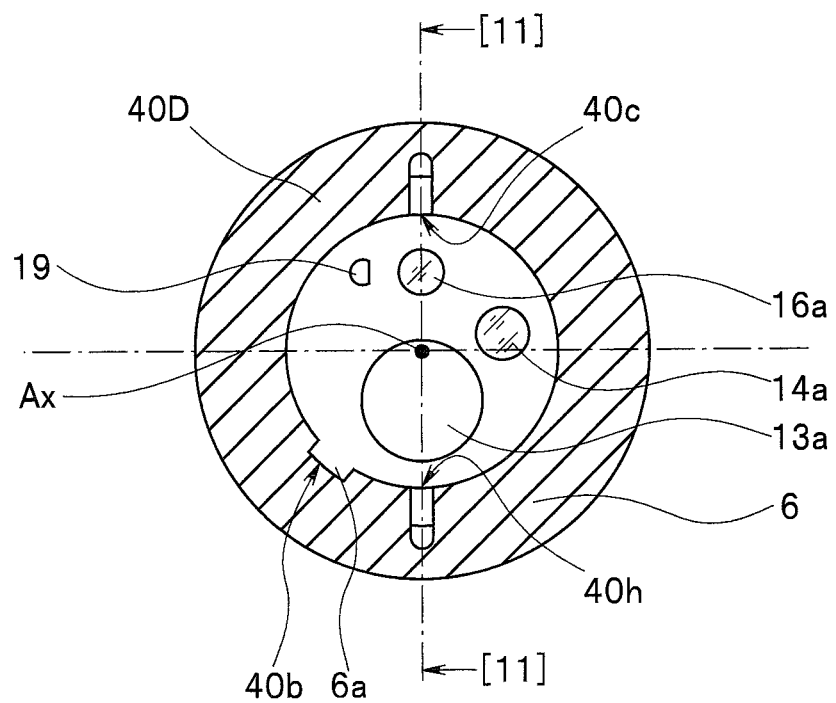
FIG. 12 is a sectional view along line [12] to [12] in FIG. 11.

FIG. 11 and FIG. 12 are views illustrating a fifth embodiment of the present invention. Of FIG. 11 and FIG. 12, FIG. 11 is a schematic sectional view illustrating a part of a distal end side of an endoscope apparatus of the present embodiment in a section along a long axis. FIG. 12 is a sectional view along line [12] to [12] in FIG. 11.

A basic configuration of the present embodiment is substantially similar to the basic configuration of the aforementioned second embodiment, and is an illustration of the mode using the endoscope distal end hood as the distal end covering portion. In the present embodiment, a mode of the endoscope distal end hood slightly differs. Accordingly, in the following explanation, component portions similar to the component portions of the aforementioned second embodiment are assigned with the same reference signs and explanation of the similar component portions is omitted.

A basic configuration of an endoscope in the endoscope apparatus of the present embodiment is similar to the basic configuration of the endoscope of the above described second embodiment (refer to FIG. 6).

An endoscope distal end hood 40D is a distal end covering portion that is fitted to the distal end portion 6 of the insertion portion 4 of the above described endoscope and is held by the distal end portion 6. A basic configuration of the endoscope distal end hood 40D is substantially similar to the basic configuration of the endoscope distal end hood of the above described second embodiment, but differs in the following point. That is, the endoscope distal end hood 40D that is the distal end covering portion which is applied in the endoscope apparatus of the present embodiment differs in the point that an air-feeding conduit opening 40h is provided in a site at an opposite side to the conduit opening 40c with the long axis Ax between the conduit opening 40c and the air-feeding conduit opening 40h, apart from the conduit opening 40c (the same mode as in the above described second embodiment) that is connected to the distal end side of the suction conduit 40a, as illustrated in FIG. 11 and FIG. 12.

The air-feeding conduit opening 40h is provided by being bored in one site of the inner face (inner surface) of the inward flange 40e, which is a site to which the outer circumferential edge portion of the distal end face of the distal end portion 6 is adjacent when the endoscope distal end hood 40D is fitted to the distal end portion 6 substantially similarly to the above described conduit opening 40c, and is an opening portion at the distal end side of the suction conduit 40a and the suction tube 40d.

Further, with the configuration, in the present embodiment, an air-feeding conduit 40k that is a third conduit different from the suction conduit which is connected to the above described air-feeding conduit opening 40h, and an air-feeding tube 43 that has one end at a distal end side connected to the air-feeding conduit 40k and extends rearward of the endoscope distal end hood 40D are included. The air-feeding tube 43 has the other end at the proximal side connected to an air-feeding and liquid-feeding apparatus 39 or an air-feeding pump not illustrated which is placed separately from the air-feeding and liquid-feeding apparatus 39, for example.

In the endoscope distal end hood 40D in the present embodiment, the respective component portions of the conduit opening 40c, the suction conduit 40a and the suction tube 40d, and the respective component portions of the air-feeding conduit opening 40h, the air-feeding conduit 40k and the air-feeding tube 43 are formed in substantially the same mode. The suction tube 40d is connected to the suction apparatus 41, and the air-feeding tube 43 is connected to the air-feeding and liquid-feeding apparatus 39 or the air-feeding pump not illustrated, respectively. The other configuration is substantially similar to the configurations of the above described second embodiment.

By the configuration, a function of causing gas as described later to flow in the air-feeding conduit 40k and the air-feeding tube 4 by an action of the above described air-feeding pump, and supplying gas into a subject via the air-feeding conduit opening 40h that is disposed adjacently to the distal end face of the insertion portion 4 is included.

It is assumed that when a procedure of treatment by ESD or the like is implemented, for example, by using the endoscope apparatus of the above described fifth embodiment configured as above, treatment to a desired treatment target site in a body cavity is performed, and liquid droplets and the like in a mist state including fat, living tissue and the like are vaporized from the treatment target site.

In this case, in the present endoscope system, the suction apparatus 41 may be automatically operated by being synchronized with timing of the above described treatment implementation. Alternatively, a user may manually operate the suction apparatus 41.

Thereupon, by the action of the suction apparatus 41, the liquid droplets and the like in the mist state including fat, living tissue and the like that are vaporized into the above described body cavity are sucked (discharged) to outside via the suction conduit 40a and the suction tube 40d from the above described conduit opening 40c.

Further, when air feeding and liquid feeding from the observation window nozzle 19 is performed, cleaning gas, liquid and the like that stay in a region between the conduit opening 40c and the observation window 16a are also sucked to the conduit opening 40c, in the distal end face of the distal end portion 6.

Furthermore, by simultaneously performing a suction operation using a suction operation button and the like included in the endoscope, the fluid and the like staying in the vicinity of the endoscope front face can be also sucked from the channel distal end opening 13a.

By the actions, the liquid droplets and the like in the mist state including fat, living tissue and the like floating in the vicinity of the observation window 16a, the cleaning gas, a liquid and the like are removed. Accordingly, an endoscopic image that is obtained by the image pickup section which is behind the observation window 16*a* and is provided inside the above described distal end portion 6 always becomes a clear image.

Here, when suction or the like by the suction apparatus 41 is performed as described above, a pressure in the body cavity changes in a direction to decrease by the suction action. Thus, when the suction action by the above described suction apparatus 41 is started in the present embodiment, the above described air-feeding and liquid-feeding apparatus 39 or the air-feeding pump not illustrated is operated automatically by being synchronized with the suction action, and gas such as carbon dioxide is supplied (fed) toward the body cavity from the air-feeding conduit opening 40*h* via the air-feeding tube 43 and the air-feeding conduit 40*k*. Note that the air feeding operation may be properly performed manually at desired timing by a user. By the action like this, the pressure in the body cavity that is decreased by the suction action of the above described suction apparatus 41 is restored.

As described above, according to the above described fifth embodiment, a similar effect to the effects of the above described respective embodiments can be obtained. Further, according to the present embodiment, the endoscope distal end hood 40D which is the distal end covering portion is configured to be provided with the air-feeding tube 43 which is connected to the above described air-feeding and liquid-feeding apparatus 39 or the air-feeding pump not illustrated, the air-feeding conduit 40*k* and the air-feeding conduit opening 40*h*, besides being provided with the suction tube 40*d* which is connected to the suction apparatus 41, the suction conduit 40*a* and the conduit opening 40*c*. Accordingly, by the configuration, the pressure in the body cavity which is decreased by the suction action by the suction apparatus 41 can be easily restored by performing the air feeding operation at proper timing, and the pressure in the body cavity can be always kept constant. Therefore, the burden on the patient that is a target of the procedure performed by using the endoscope apparatus can be reduced.

Note that in the present embodiment, the mode may be adopted, in which the protruded portion is included by using the annular member 42 shown in the one modification in the aforementioned first embodiment, instead of providing the protruded portion 6*a* at the distal end portion 6.

Further, in the present embodiment, a mode of placement of the protruded portion at the distal end portion side and the groove portion at the endoscope distal end hood side may be made a mode in which the protruded portion and the groove portion are exchanged respectively, that is, a mode in which the recessed groove is provided at the distal end portion side, and the protruded portion is provided at the distal end covering portion side (the endoscope distal end hood side).

Furthermore, a structure of the endoscope distal end hood of the present embodiment can be easily applied directly to the over tube or the like that is the distal end covering portion of the above described first embodiment.

It is needless to say that the present invention is not limited to the aforementioned embodiments, but it is possible to carry out various modifications and applications within the range without departing from the gist of the invention. Further, the above described embodiments include the inventions in various stages, and various inventions can be extracted by appropriate combinations in the plurality of components which are disclosed. For example, even when some components are deleted from all the components shown in the above described one embodiment, if the problem to be solved by the invention can be solved, and the effect of the invention can be obtained, the configuration from which the components are deleted can be extracted as the invention. Further, the components across the different embodiments may be properly combined. The invention is not restricted by a specific embodiment of the invention except for being limited by the accompanying claims.

INDUSTRIAL APPLICABILITY

The present invention can be applied not only to an endoscope control apparatus in the medical field, but also to an endoscope control apparatus in the industrial field.

What is claimed is:

1. An endoscope apparatus, comprising:
 an endoscope insertion portion configured to be inserted into a subject, the endoscope insertion portion comprising:
  a distal end portion; and
  a second conduit configured to cause a proximal end side and a distal end side of the endoscope insertion portion to communicate with each other, the second conduit being configured for insertion of a treatment instrument into an inside of the subject from a second opening on a distal end face of the distal end portion; and
 an overtube configured to cover at least an outer periphery of the distal end portion of the endoscope insertion portion, the overtube comprising a first conduit provided with a first opening, the first conduit being configured to cause an inside of the subject and an outside of the subject to communicate with each other;
 wherein the overtube having one of a groove and a projection and the endoscope insertion portion having an other of the groove and the projection, the groove and the projection being configured to mate together to define an angular orientation of the first opening relative to the distal end portion about a longitudinal axis of the distal end portion when the overtube covers at least the outer periphery of the distal end portion, and
 a first virtual straight line defines a first half and a second half of the distal end face, the first virtual straight line being orthogonal to a virtual second straight line extending from a first center of the first opening, a second center of the second opening being disposed on the second half of the distal end face and the first opening being on a periphery of the first half.

2. The endoscope apparatus according to claim 1, wherein the second center of the second opening is located on the virtual first straight line.

3. The endoscope apparatus according to claim 1, wherein the first conduit is inserted through an inside of the endoscope insertion portion at a proximal end side of the endoscope insertion portion, the first conduit being exposed to outside of the endoscope insertion portion at a distal end side of the endoscope insertion portion, and the overtube holds an opening portion provided in a distal end of the first conduit.

4. The endoscope apparatus according to claim 1, wherein the first opening of the first conduit opens in an inner surface of the overtube.

5. The endoscope apparatus according to claim 4, wherein the first opening of the first conduit further opens in an outer surface of the overtube.

6. The endoscope apparatus according to claim 1, wherein the first opening of the first conduit opens in an inner surface and an outer surface of the overtube.

7. The endoscope apparatus according to claim 1, wherein the other of the groove and the projection is formed on an attachment member separately from the endoscope insertion portion, and is configured to be attachable to and detachable from the distal end portion.

8. The endoscope apparatus according to claim 7 wherein the attachment member is formed in an annular shape having the projection directed outward on a part of an outer circumferential face.

9. The endoscope apparatus according to claim 1, wherein:
the overtube further comprising a third conduit having a third opening for supplying gas into the inside of the subject from the outside of the subject, the third conduit being different from the first conduit; and
the endoscope apparatus further comprising an air-feeding pump provided at the outside of the subject and configured to supply gas to the third conduit,
wherein the first conduit is configured to suck a fluid generated from the inside of the subject to the outside of the subject via the first opening.

10. The endoscope apparatus according to claim 1, wherein the endoscope insertion portion further comprising an observation window through which an optical image of the inside of the subject is acquired, a third center of the observation window being disposed on the distal end face on the second virtual straight line.

11. The endoscope apparatus according to claim 10, wherein the first opening, the second opening and the third center are on the second virtual straight line with the third center being between the first opening and the second opening.

12. An endoscope system, comprising:
an endoscope insertion portion configured to be inserted into a subject the endoscope insertion portion comprising:
a distal end portion; and
a second conduit configured to cause a proximal end side and a distal end side of the endoscope insertion portion to communicate with each other, the second conduit being configured for insertion of a treatment instrument into an inside of the subject from a second opening on a distal end face of the distal end portion;
an overtube configured to cover at least an outer periphery of the distal end portion of the endoscope insertion portion, the overtube comprising a first conduit provided with a first opening, the first conduit being configured to cause an inside of the subject and an outside of the subject to communicate with each other;
wherein the overtube having one of a groove and a projection and the endoscope insertion portion having an other of the groove and the projection, the groove and the projection being configured to mate together to define an angular orientation of the first opening relative to the distal end portion about a longitudinal axis of the distal end portion when the overtube covers at least the outer periphery of the distal end portion;
a treatment instrument configured to be inserted into the subject from the outside of the subject via the second conduit;
a high-frequency current generator configured to cauterize a part of the subject by giving energy to the treatment instrument in the subject; and
a suction pump to which the first conduit connects to discharge mist generated when the high-frequency current generator cauterizes a part of the subject to the outside of the subject from the inside of the subject via the first conduit,
wherein the endoscope insertion portion includes an observation optical system configured to acquire an optical image of the inside of the subject, and
a first virtual straight line defines a first half and a second half of the distal end face, the first virtual straight line being orthogonal to a virtual second straight line extending from a first center of the first opening, a second center of the second opening being disposed on the second half of the distal end face and the first opening being on a periphery of the first half.

13. The endoscope system according to claim 12, wherein the second opening is located on the virtual first straight line.

14. The endoscope system according to claim 12, wherein the endoscope insertion portion further comprising an observation window through which an optical image of the inside of the subject is acquired, a third center of the observation window being disposed on the distal end face on the second virtual straight line.

15. The endoscope system according to claim 14, wherein the first opening, the second opening and the third center are on the second virtual straight line with the third center being between the first opening and the second opening.

* * * * *